US010332014B2

(12) United States Patent
Wasserkrug et al.

(10) Patent No.: US 10,332,014 B2
(45) Date of Patent: Jun. 25, 2019

(54) CONCISE STATE MODEL FOR OPERATIONAL OPTIMIZATION OF WASTEWATER TREATMENT UNIT(S)

(71) Applicant: International Business Machines Corporation, Armonk, NY (US)

(72) Inventors: Segev E Wasserkrug, Haifa (IL); Alexander Zadorojniy, Haifa (IL); Sergey Zeltyn, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 842 days.

(21) Appl. No.: 14/835,771

(22) Filed: Aug. 26, 2015

(65) Prior Publication Data

US 2017/0061309 A1     Mar. 2, 2017

(51) Int. Cl.
   *G06N 5/04*     (2006.01)
   *G06N 7/00*     (2006.01)
   (Continued)

(52) U.S. Cl.
   CPC ............ *G06N 7/005* (2013.01); *C02F 3/006* (2013.01); *G01N 33/18* (2013.01); *G01N 33/182* (2013.01); *G06Q 40/12* (2013.12); *C02F 2209/006* (2013.01); *C02F 2209/008* (2013.01); *C02F 2209/16* (2013.01); *C02F 2209/18* (2013.01); *C02F 2209/22* (2013.01); *C02F 2209/40* (2013.01); *G06N 5/04* (2013.01)

(58) Field of Classification Search
   CPC ........................................................ G06N 5/04
   USPC ................................................... 706/52, 45
   See application file for complete search history.

(56) References Cited

U.S. PATENT DOCUMENTS

| 8,012,352 B1 | 9/2011 | Giraldo et al. |
| 8,293,097 B2 | 10/2012 | Bowers, Jr. |
| 8,308,944 B2 | 11/2012 | Horst |

FOREIGN PATENT DOCUMENTS

| CN | 201110135706 | 2/2013 |
| WO | 2011131806 | 10/2011 |

OTHER PUBLICATIONS

Lobbrecht, et al., Applications of Neural Networks and Fuzzy Logic to Integrated Water Management, Project Report, Delft Hydroinformatics, Oct. 2002, pp. 1-185.*

(Continued)

*Primary Examiner* — Wilbert L Starks
(74) *Attorney, Agent, or Firm* — G.E Eherlich

(57) ABSTRACT

A method for wastewater treatment that comprises receiving influent readings from sensors located along influent stream(s) of a wastewater treatment unit, effluent readings from sensors located along effluent stream(s) of the wastewater treatment unit, a feedback flow variable calculated according to a state of a feedback flow channel between an effluent output and an influent input, analyzing the influent readings and the effluent readings to extract an influent flow variable, a total nitrogen at effluent variable and a total phosphorus at effluent variable, and calculating control instructions to control the wastewater treatment unit by assigning a combination of a cost variable reflecting a treatment cost for treating the influent stream(s), a time period, the influent flow variable, the total nitrogen at effluent variable, the total phosphorus at effluent variable, and the feedback flow variable in a state space of the wastewater treatment unit.

19 Claims, 3 Drawing Sheets

Figure 1:
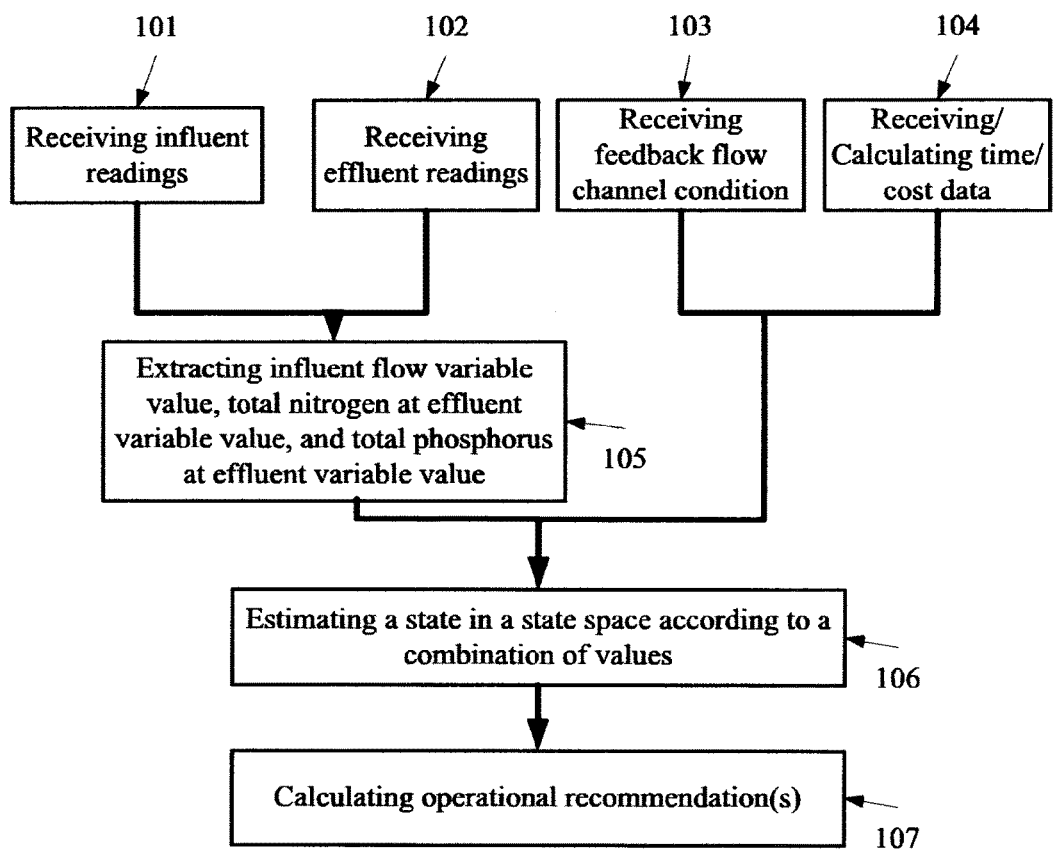

(51) Int. Cl.
*G01N 33/18* (2006.01)
*G06Q 40/00* (2012.01)
*C02F 3/00* (2006.01)

(56) References Cited

OTHER PUBLICATIONS

Alsheikh, et al., Markov Decision Processes With Applications in Wireless Sensor Networks: A Survey, IEEE Communication Surveys and Tutorials, vol. 17, No. 3, Apr. 7, 2015, pp. 1239-1267.*

Yang, et al., Water Network Optimization with Wastewater Regeneration Models, Industrial & Engineering Chemistry Research 53, 2014, pp. 1-36.*

Alsheikh, et al., Markov Decision Processes With Applications in Wireless Sensor Networks: A Survey, IEEE Communication Surveys and Tutorials, vol. 17, No. 3, Apr. 7, 2015, pp. 1239-1267 (Year: 2015).*

Xiupeng Wei., "Modeling and optimization of wastewater treatment process with a data-driven approach", Lowa research Online, The University of Lowa's Institutional Respository, May 2013.

Disclosed Anonymously., "System and method for efficient operations of wastewater treatment plants through monitoring, modeling, prediction and optimization", An IP.com Prior Art Database Technical Disclosure, Jun. 25, 2014.

* cited by examiner

CONCISE STATE MODEL FOR OPERATIONAL OPTIMIZATION OF WASTEWATER TREATMENT UNIT(S)

FIELD AND BACKGROUND OF THE INVENTION

The present invention, in some embodiments thereof, relates to optimization and, more specifically, but not exclusively, to processes and systems to automatically provide recommendations how to optimize the performance of a wastewater treatment plant.

Wastewater treatment plants are complex systems that have to deal with constantly changing inflow conditions. Consequently, theses wastewater treatment plants are difficult to operate. Nowadays many wastewater treatment plants are operated based on the operators knowledge and feelings, because in lot of cases the relevant data needed for an appropriate operation is not known and/or if the data is known the operator cannot interpret the data correctly. An optimization especially in terms of cost takes rarely place and when takes, just partially, due to the above mentioned reasons.

In order to get a better understanding of wastewater treatment plants, some models have been developed that try to simulate these wastewater treatment plants. One of these models is the "Activated sludge models ASM1, ASM2 and ASM3 published by IWA Publishing in 2000.

SUMMARY OF THE INVENTION

According to some embodiments of the present invention, there is provided a method for wastewater treatment. The method comprises receiving influent readings from a plurality of influent sensors located along at least one influent stream of a wastewater treatment unit, analyzing the influent readings to extract an influent flow variable values, receiving effluent readings from a plurality of effluent sensors located along at least one effluent stream of the wastewater treatment unit, analyzing the effluent readings to extract a total nitrogen at effluent variable value and a total phosphorus at effluent variable value, receiving a feedback flow variable value calculated according to a condition of a feedback flow channel between an effluent output and an influent input, and calculating control instructions to control the wastewater treatment unit by estimating a state in a state space of the wastewater treatment unit according to a combination of a cost variable value reflecting a treatment cost for treating the at least one influent stream, a time period, the influent flow variable value, the total nitrogen at effluent variable value, the total phosphorus at effluent variable value, and the feedback flow variable value.

Optionally, the state space is defined according to a Markov decision process (MDP) framework.

Optionally, the state space is defined according to a constrained Markov decision process (CMDP) framework.

More optionally, the constrained Markov decision process framework is generated by calculating transition probability matrices by estimation a probability of transitioning from each state of the wastewater treatment unit to another state.

More optionally, the estimation is performed by an analysis historical reading of sensors and historical operation data of a plurality of wastewater treatment units.

More optionally, the calculating control instructions to control the wastewater treatment unit comprises calculating a policy for the wastewater treatment unit by the transition probability matrices and a set of constraints.

Optionally, the calculating control instructions to control the wastewater treatment unit is set for minimizing a total cost of a treatment process while complying with received regulatory requirements.

Optionally, the cost variable is a total cost variable summarizing at least some members of the following group: an electricity cost, a sludge disposal cost, and chemical costs.

Optionally, the control instructions are calculated while taking into account total nitrogen at effluent constraint and total phosphorus at effluent constraint.

Optionally, the influent readings and the effluent readings are received from a supervisory control and data acquisition (SCADA) system of the wastewater treatment unit and the control instructions are sent to the SCADA system.

Optionally, the calculating is performed using a CPLEX solver.

Optionally, the control instructions comprise an internal recycle (IR) pump rate change instructions.

Optionally, the control instructions comprise a flow pump rate instructions.

Optionally, the control instructions comprise instructions to adapt dissolved oxygen level in a reactor of the wastewater treatment unit.

According to some embodiments of the present invention, there is provided a system for wastewater treatment. The system comprises an interface for receiving: influent readings from a plurality of sensors located along at least one influent stream of a wastewater treatment unit, effluent readings from a plurality of sensors located along at least one effluent stream of the wastewater treatment unit, and a feedback flow channel variable value calculated according to a state of a feedback flow channel between an effluent output and an influent input a memory storing a code, a processor adapted to execute the following code instructions in the code: code instructions for analyzing the influent readings to estimate an influent flow variable value, code instructions for analyzing the effluent readings to estimate a total nitrogen at effluent variable value and a total phosphorus at effluent variable value, and code instructions for calculating control instructions to control the wastewater treatment unit by estimating a state in a state space of the wastewater treatment unit according to a combination of a cost variable value reflecting a treatment cost for treating the at least one influent stream, a time period value, the influent flow variable value, the total nitrogen at effluent variable value, the total phosphorus at effluent variable value, and the feedback flow variable value.

Optionally, the state space is defined according to a constrained Markov decision process (CMDP) framework.

Optionally, the influent readings and the effluent readings are received from a supervisory control and data acquisition (SCADA) system of the wastewater treatment unit and the control instructions are sent to the SCADA system.

Optionally, the cost variable is a total cost variable summarizing at least some members of the following group: an electricity cost, a sludge disposal cost, and chemical costs.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions,

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 2:
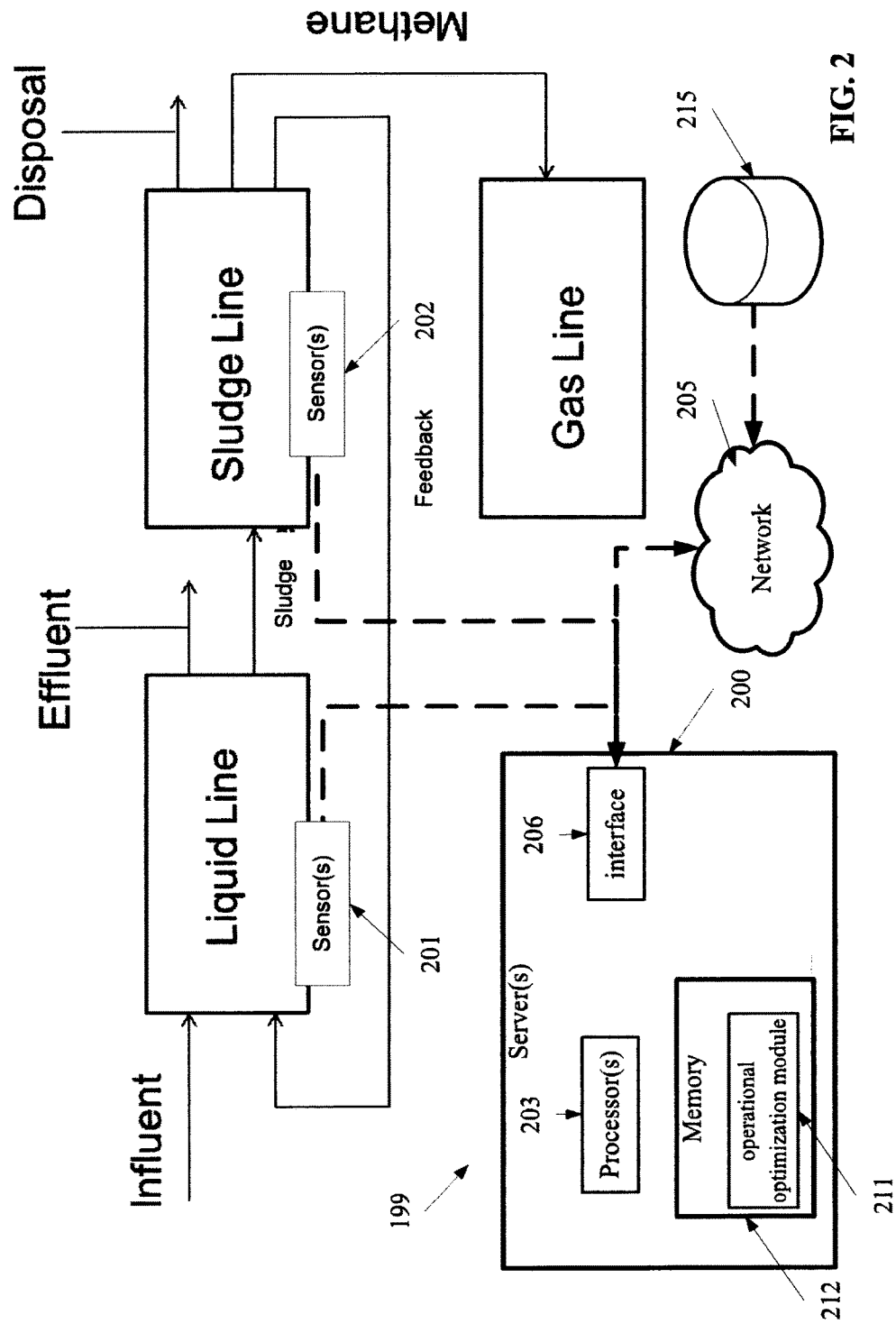
Figure 3:
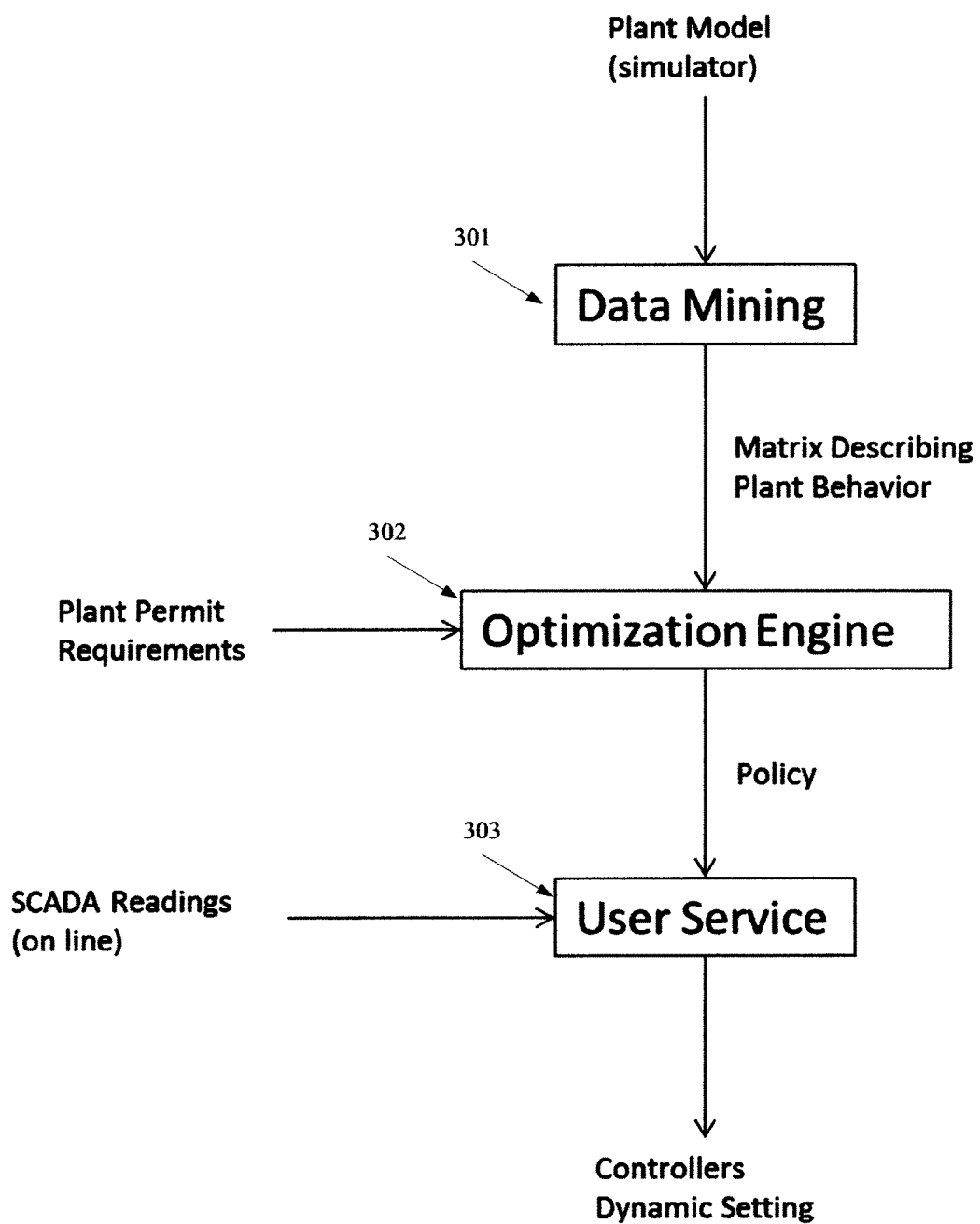

In the drawings:

FIG. 1 is a flowchart of an exemplary process of a method for optimizing a wastewater treatment based on the above set of variables, according to some embodiments of the present invention;

FIG. 2 is a schematic illustration of lines of an exemplary wastewater treatment unit, database(s) or a data interface of a control system of the exemplary wastewater treatment unit, and a system for optimizing a wastewater treatment based on a set of variables, for instance by implementing the process depicted in FIG. 1, according to some embodiments of the present invention; and FIG. 3 is a flowchart of an exemplary process of calculating control instructions based on a set of variables, according to some embodiments of the present invention.

DESCRIPTION OF SPECIFIC EMBODIMENTS OF THE INVENTION

The present invention, in some embodiments thereof, relates to optimization and, more specifically, but not exclusively, to processes and systems to automatically provide recommendations how to optimize the performance of a wastewater treatment plant.

According to some embodiments of the present invention, there are provided methods and systems for minimizing a total cost of a treatment process of a wastewater treatment unit by calculating instructions to control the wastewater treatment unit by estimating a state in a state space of the wastewater treatment unit according to a reduced set of variables. The reduced set of variables was surprisingly found by the inventors and includes a cost variable reflecting a treatment cost for treating the influent stream(s) by the wastewater treatment unit, a time period of a treatment process, the influent flow variable of the wastewater treatment unit, the total nitrogen at effluent variable of the wastewater treatment unit, the total phosphorus at effluent variable of the wastewater treatment unit, and the feedback flow variable of the wastewater treatment unit.

Optionally, the state space is used by a constrained Markov decision process (CMDP) framework or a Markov decision process (MDP), for instance when the constrains are null. For brevity, CMDP and MDP may be referred to herein as interchangeably. The MDP transition probability matrix is optionally calculated by historical reading of sensors and historical operation data of wastewater treatment unit(s) and a model of the wastewater treatment unit. The control instructions are optionally selected from a policy generated by solving CMDP problem using for example Linear Programming algorithms.

Some of the variable values of the reduced set are optionally extracted in real time from readings of sensors which are distributed in the wastewater treatment unit, for example as received from the supervisory control and data acquisition (SCADA) system of the wastewater treatment unit. The control instructions are optionally provided to the SCADA system of the wastewater treatment unit.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

A common wastewater treatment unit (WWTU), such as a wastewater treatment plant (WWTP) or any other wastewater treatment device or system, for brevity referred to herein as a WWTU, treats incoming wastewater, for example sewage, referred to as influent, to a level, for example a level set according to local regulations or protocols. The two main outputs of a WWTU are treated fluid, referred to as effluent, and treated bio solids, referred to as sludge. The properties of the effluent and the sludge emitted from a WWTU usually comply with the regulatory constraints which are specific to the location of the WWTU. An example of such a constraint is that a monthly/daily average of total nitrogen in the effluent is less than 15 milligram per liter [mg/l]. Treating the wastewater is carried out in multiple steps, in which the wastewater is treated by biological, physical (e.g. mechanical) and/or chemical sub-processes. Moreover, there are iterative sub-processes so that the same wastewater portion visits some of the sub-process multiple times. This complexity renders the total operating costs of a water treatment process high. The total operating costs includes electricity cost required to treat wastewater (including pumping) throughout the water treatment process, a cost of various chemicals required in the water treatment process, and disposal costs of the sludge.

Today, most of the WWTUs are operated in a conservative and inefficient risk-averse mode, without the ability to quantify a risk, or truly minimize costs. Some sub-processes are optimized locally; however, a local optimum of a certain sub-process may have a negative effect on one or more other sub-processes which are not taken into account. Such local optimization may even have an adversely effect on the process as a whole.

Some embodiments of the present invention provide a technical solution to the problem of optimizing the water treatment process as a whole. This technical solution is based on a concise state representation of a WWTU optimization model which reduces dramatically the number of optional states to a computational efficient level for efficiently calculating recommendations or control instructions for the WWTU.

In particular, hundreds of state variables are required to represent a full state of a WWTU. Therefore, finding a reduced set of variables for a state representation is desired. Inventors surprisingly identified a reduced set of state variables after a conducting various experiments in a number of different WWTUs. These state variables includes the following:

a feedback flow variable—a variable that the value thereof indicates at least a presence or an absence of an active feedback flow channel between an effluent output, for example in a sludge line, and an influent input in a liquid line which optionally precedes the sludge line, influent flow variable—for example values measured by sensors at the input of liquid line or at the sludge line when centrifuge is on or off, a total cost variable indicating a total cost of treating the influent, for example a sum of at least the cost of biological, physical and chemical sub-processes, a time interval variable—a variable that the value thereof indicates a period of a treating process during a day (i.e. as electricity tariff vary during the day, a total nitrogen at effluent variable—for example values measured at the effluent output, and a total phosphorus at effluent variable—for example values measured at the effluent output.

Inventors surprisingly discovered that the above reduced set of variables can be used instead of hundreds of variables in a regular model for real time operational optimization purposes, for instance by generating operational recommendations or control instructions which may be referred to herein interchangeably.

It should be noted that the there are two conflicting constraints in the model, total phosphorus and total nitrogen. Optionally, when a total phosphorus and nitrogen constraints are satisfied in the model, it is assumed that the rest of constraints are satisfied with margins and hence no explicit modeling of all constrains is needed (regardless of whether additional constraints are added or not).

Reference is now made to FIG. 1 which is a flowchart 100 of an exemplary process of a method for optimizing a wastewater treatment based on the above set of variables, according to some embodiments of the present invention. Reference is also made to FIG. 2, which is a schematic illustration of lines of an exemplary WWTU, database(s) 215 or a data interface of a control system of the WWTU, and a system 199 for optimizing a wastewater treatment based on values of the above reduced set of variables, for instance by implementing the process depicted in FIG. 1, according to some embodiments of the present invention.

The system 199 is optionally implemented by one or more servers 200 (or computing devices and/or virtual machines) with one or more processors 203. The system 199 further includes an interface 106 for receiving readings of sensor(s) located to monitor a value of influent flow variable, for instance sensor(s) 201 and sensor(s) which are located to monitor a value of total nitrogen at effluent variable and a value of a total phosphorus at effluent variable, for instance sensor(s) 202. The sensors are part of a WWTU operating with coded signals over communication channels so as to provide control of WWTU equipment, e.g. supervisory control and data acquisition (SCADA) system.

The readings may be received directly from the sensors or via a proxy or an input device. The interface 106 may also be used for acquiring data from database(s) 215 associated with the WWTU (or proxy units of the WWTU) (not shown), optionally via a network 205 such as the internet. The acquired data may be a total cost or fractions thereof, a time period, and a value of a feedback flow variable. The system 199 further includes or connected to a memory 212 hosting an operational optimization module 211 executed by the processors 203 for calculating recommendations or control instructions(s), for example as described below and depicted in FIG. 1.

In use, as shown at 101-102, readings of the sensors 201, 202 are received and read. This allows extracting the influent flow variable values, the total nitrogen at effluent variable values, and the total phosphorus at effluent variable values, as shown at 105. As shown at 103-104 the feedback flow channel variable values and the total cost variable values and/or the time interval variable values are acquired or received, for example via the interface 206, optionally from the database(s) 215.

Now, as shown at 106, a state in a state space is estimated according to a combination of the set of variable values acquired in 101-105, for example to a constrained Markov decision process (MDP) framework.

For example, a CMDP framework is used for the estimation. Reference is now made to a mathematical explanation of a CMDP framework for performing the estimation, see for example Puterman, M.: Markov decision processes: discrete stochastic dynamic programming John Wiley & Sons, Inc. New York, N.Y., USA (1994) which is incorporated herein by reference. The MDP may be defined as a 4-tuple {X; U; P; c} where X denotes a finite set of states {0, . . . , n−1} U a finite set of actions [0, . . . , k−1], P denotes a transition probability function $X^2 \times U \rightarrow [0; 1]$ is, and c denotes a cost function $X \times U \rightarrow R$ is. The probability of a transition from state x to state y when the action u is chosen is specified by function P and denoted by P(y|x,u). A cost associated with selecting the action u when in state x equals c(x,u). Initial states are denoted $x_0$.

Time is discrete, and in each time unit (denoted t), $x_t$ denotes a random variable that equals the state at time t. Similarly, $u_t$ denotes a random variable that equals the action selected at time t. A (stationary) policy is a function π: $X \times U \rightarrow [0,1]$ such that $\Sigma_u \pi(x,u)=1$ for every $x \in X$. A policy controls the action selected in each state as follows: the probability of selecting action u in state x equals π(x,u). The goal is to find a policy that minimizes the cost C(π) defined below.

Optionally a discounted cost model is used where in the discounted cost model, the parameter $\beta \in (0,1)$ specifies a rate by which future costs are reduced. where $P^\pi(x_t=x; u_t=u)$ denote a probability of the event $x_t=x$ and $u_t=u$ when the initial state equals $x_0$ (once set, remains unchanged and omitted from the notation) and the policy is π. The infinite horizon discounted expected cost C(π) is defined by the following equation:

$$C(\pi) \triangleq (1-\beta) \cdot \sum_{t=0}^{\infty} \beta^t \cdot E^\pi[c(x_t, u_t)].$$

Equation 1

Every policy π. induces a probability measure over the state-action pairs. This probability measure may be referred to as an occupation measure corresponding to π and denoted by $p^\pi$ such that:

$$\rho^\pi(x,u) \triangleq (1-\beta) \cdot \Sigma_{t=0}^{\infty} \beta^t \cdot P^\pi(x_t=x, u_t=u).$$

Equation 2:

Given an occupation measure p(x,u) over X×U, the policy $\pi^p$ induced by p is defined as follows:

$$\pi_\rho(x,u) \triangleq \rho(x,u)/\Sigma_u \rho(x,u').$$

Equation 3:

Where when $\Sigma_u \rho(x,u')=0$ then one may define $\pi^p(x,u)$ arbitrarily as long as $\Sigma_u \pi^p(x,u)=1$. A cost may be rewritten using occupation measures notations as follows:

$$C(\pi) \triangleq \sum_{x \in X, u \in U} c(x, u) \cdot \rho^\pi(x, u).$$

Equation 4

Based on the above, a constrained MDP, see for example Altman, E.: Constrained Markov decision processes, vol. 7. CRC Press (1999) which is incorporated herein by reference, is an MDP with additional input consisting of a set of constraints L (|L|=l), associated with a cost function vector $\vec{d}: X \times U \rightarrow \mathbb{R}^l$ and a vector of parameters $\vec{\alpha}$. The cost $D^i(\pi)$ of π for any constraint $i \in L$ is defined similarly to C(π):

$$E^\pi[d^i(s_t,u_t)]=(1-\beta) \cdot \beta^t \Sigma_{x \in X, u \in U} d^i(s,u) \cdot P^\pi(s_t=s, u_t=u).$$

Equation 5:

The additional input defines the constraints $\overline{D}(\pi) \leq \overline{\alpha}$ that a feasible policy must satisfy. The optimization problem in CMDP($\bar{\alpha}$) is to find a policy that minimizes C($\pi$) subject to the constraints $\ddot{D}(\pi) \le \alpha$ where the inequality is interpreted component wise.

This allows, as shown at 107, calculating an operational recommendation(s) for improving the treatment process of the WWTU, for example by taking a decision based on the outcome of estimating a state in the state space according to a combination of values of the reduced set of variables acquired in 101-105. An improvement may be a cost reduction, or effluent quality improvement or both. The operational recommendations are optionally real time instructions to controllers of the equipment of the monitored WWTU, for instance a WWTP. Examples of control instructions are a DO set point instruction, an internal recycle (IR) pump rate change instructions, a WAS flow pump rate instructions and/or the like.

The process depicted in 101-107 is optionally iteratively repeated to provide a dynamic real time control for minimizing a total cost of a treatment process while complying with the regulatory requirements.

The operational recommendations are calculated while taking into account total nitrogen at effluent and total phosphorus at effluent constraints.

For example, when referring to the above mathematical explanation of an CMDP framework for performing the estimation, the following action variables may be used (v1-v10 are used to indicate values):

1. DO_SP $\in$[v1, v2, v3, v4] [mg/l] is an action variable controlling a dissolved oxygen level in a WWTU reactor.
2. WAS Flow $\in$[v5, v6, v7, v8] [m$^3$/hour] is an action variable controlling a pump that regulates a WAS flow (flow from the liquid line (LL) to sludge line (SL) block).
3. REC_SP $\in$[v9, v10, v11] [m$^3$/hour] is an action variable controlling a pump that regulates a feedback flow inside the LL.

In addition, the above mentioned reduced set of variables may be used:

1. F_B$\in$[off on].
2. I_F$\in$[low, med, high]
3. Cost $\in$[low, med, high]—The cost can be negative when biogas-produced electricity is used since there are other pats of the plant where this electricity can be used and which are not optimized.
4. TimePeriod $\in$[exp, med, cheap]—for example when there are three different price intervals over the course of the day. Intervals and prices may be fixed per month or week.
5. E_TN $\in$[low, med, high]
6. E_TP $\in$[low, med, high]

where there are two conflicting constraints in the model: total phosphorus and total nitrogen. Note that there are more constraints in the permit, however when total phosphorus and nitrogen constraints are satisfied, the rest of the constraints are satisfied with larger margins. For example, the constraints are defined as follows (value in mg/l is exemplary):

$$d(E\_TN)^T \cdot \rho(E\_TN) \le 15 \text{ [mg/l]} \qquad 1.$$

$$d(E\_TP)^T \cdot \rho(E\_TP) \le 1 \text{ [mg/l]}. \qquad 2.$$

A transition probabilities matrix is generated for the WWTU (LL, SL, and gas line (GL) together) and the cost is a total cost of operating LL, SL, and GL together. As control variables of the SL and GL are not used, it is sufficient to add only LL variables to the state space. A dual LP formulation may be used for the CMDP. This formulation can be solved using a CPLEX solver.

Reference is now also made to FIG. 3, which is a flowchart of an exemplary process of calculating an operational recommendations or control instructions based on an estimation of a state in a state space according to a combination of values of the above set of variables, according to some embodiments of the present invention. First, as shown at 301, a data mining process is held, for example by analyzing historical reading of sensors and historical operation data of a plurality of WWTUs. This data reflects patterns of historical sensor readings and logged operation data. The data mining process and a model of the WWTU, for instance an existing WWTU simulator, are used to generate transition probability matrices of an MDP which describes a plant behavior, for example a probability of transitioning from each state of the WWTU (or each of some of the states) to another state (or to at least some of the states) in a single step, dependent on the actions chosen by the controllers. As shown at 302, the transition probability matrices, together with constraints, such as regulatory requirements, are provided as an input to an optimization engine which calculates state-based recommendations. for the respective WWTU. The state-based recommendations, referred to herein as a. policy, are optionally an optimal/near-optimal state-based policy. 301 and/or 302 may be conducted in advance, for instance as a preprocessing thread held before the process depicted in FIG. 1 starts. Block 303 depicts a real time control loop where readings and data about the state of the WWTU is received for calculation operational recommendations for the WWTU. Optionally, the recommendations are time-based as derived from a time dependent state. The operational recommendations are used for automatically calculating instructions to the corresponding controllers of the equipment of the WWTU with respect to the inputted policy. Optionally, the optimization problem is minimizing a total cost while complying with the regulatory requirements, see for example above described equation 4.

The methods as described above are used in the fabrication of integrated circuit chips.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant systems and processes will be developed and the scope of the term a unit, a sensor, a processor, a WWTU, and a WWTU equipment is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for controlling wastewater treatment unit for an optimized operation with improved performance, comprising:
   receiving influent readings from a plurality of influent sensors located along at least one influent stream of a wastewater treatment unit;
   analyzing said influent readings to extract an influent flow variable values;
   receiving effluent readings from a plurality of effluent sensors located along at least one effluent stream of said wastewater treatment unit;
   analyzing said effluent readings to extract a total nitrogen at effluent variable value and a total phosphorus at effluent variable value;
   receiving a feedback flow variable value calculated according to a condition of a feedback flow channel between an effluent output and an influent input;
   generating control instructions to control said wastewater treatment unit by estimating a state in a state space of said wastewater treatment unit according to a combination of a cost variable value reflecting a treatment cost for treating said at least one influent stream, a time period, said influent flow variable value, said total nitrogen at effluent variable value, said total phosphorus at effluent variable value, and said feedback flow variable value, said control instructions are calculated to optimize a performance of said wastewater treatment unit through at least one of increasing effluent quality and reducing operational costs; and
   controlling, using said control instructions, an operation of at least one of an internal recycle (IR) pump, a flow pump and adaptation of dissolved oxygen level in a reactor of said wastewater treatment unit;
   wherein said state space is defined according to a Markov decision process (MDP) framework.

2. The method of claim 1, wherein said state space is defined according to a constrained Markov decision process (CMDP) framework.

3. The method of claim 2, wherein said constrained Markov decision process framework is generated by calculating transition probability matrices by estimation a probability of transitioning from each state of said wastewater treatment unit to another state.

4. The method of claim 3, wherein said estimation is performed by an analysis historical reading of sensors and historical operation data of a plurality of wastewater treatment units.

5. The method of claim 3, wherein said calculating control instructions to control said wastewater treatment unit comprises calculating a policy for said wastewater treatment unit by said transition probability matrices and a set of constraints.

6. The method of claim 1, wherein said calculating control instructions to control said wastewater treatment unit is set for minimizing a total cost of a treatment process while complying with received regulatory requirements.

7. The method of claim 1, wherein said cost variable is a total cost variable summarizing at least some members of the following group: an electricity cost, a sludge disposal cost, and chemical costs.

8. The method of claim 1, wherein said control instructions are calculated while taking into account total nitrogen at effluent constraint and total phosphorus at effluent constraint.

9. The method of claim 1, wherein said influent readings and said effluent readings are received from a supervisory control and data acquisition (SCADA) system of said wastewater treatment unit and said control instructions are sent to said SCADA system.

10. The method of claim 1, wherein said calculating is performed using a CPLEX solver.

11. The method of claim 1, wherein said control instructions comprises an internal recycle (IR) pump rate change instructions.

12. The method of claim 1, wherein said control instructions comprises a flow pump rate instructions.

13. The method of claim 1, wherein said control instructions comprises instructions to adapt dissolved oxygen level in a reactor of said wastewater treatment unit.

14. A non transitory computer readable medium comprising computer executable instructions adapted to perform the method of claim 1.

15. A system for controlling wastewater treatment unit for an optimized operation with improved performance, comprising:
an interface for receiving:
influent readings from a plurality of sensors located along at least one influent stream of a wastewater treatment unit,
effluent readings from a plurality of sensors located along at least one effluent stream of said wastewater treatment unit, and
a feedback flow channel variable value calculated according to a state of a feedback flow channel between an effluent output and an influent input
a memory storing a code;
a processor adapted to execute the following code instructions in said code:
code instructions for analyzing said influent readings to estimate an influent flow variable value,
code instructions for analyzing said effluent readings to estimate a total nitrogen at effluent variable value and a total phosphorus at effluent variable value,
code instructions for generating control instructions to control said wastewater treatment unit by estimating a state in a state space of said wastewater treatment unit according to a combination of a cost variable value reflecting a treatment cost for treating said at least one influent stream, a time period value, said influent flow variable value, said total nitrogen at effluent variable value, said total phosphorus at effluent variable value, and said feedback flow variable value, said control instructions are calculated to optimize a performance of said wastewater treatment unit through at least one of increasing effluent quality and reducing operational costs, and
code instructions to control, using said control instructions, an operation of at least one of an internal recycle (IR) pump, a flow pump and adaptation of dissolved oxygen level in a reactor of said wastewater treatment unit;
wherein said state space is defined according to a Markov decision process (MDP) framework.

16. The system of claim 15, wherein said state space is defined according to a constrained Markov decision process (CMDP) framework.

17. The system of claim 15, wherein said influent readings and said effluent readings are received from a supervisory control and data acquisition (SCADA) system of said wastewater treatment unit and said control instructions are sent to said SCADA system.

18. The system of claim 15, wherein said cost variable is a total cost variable summarizing at least some members of the following group: an electricity cost, a sludge disposal cost, and chemical costs.

19. A computer program product for controlling wastewater treatment unit for an optimized operation with improved performance, the computer program product comprising a non transitory computer readable storage medium having program instructions embodied therewith, the program instructions executable by at least one processor of at least one server to cause the server to:
receive, at said at least one server, influent readings from a plurality of sensors located along at least one influent stream of a wastewater treatment unit;
analyze, at said at least one server, said influent readings to extract an influent flow variable values;
receive, at said at least one server, effluent readings from a plurality of sensors located along at least one effluent stream of said wastewater treatment unit;
analyze, at said at least one server, said effluent readings to extract a total nitrogen at effluent variable value and a total phosphorus at effluent variable value;
receive, at said at least one server, a feedback flow variable value calculated according to a condition of a feedback flow channel between an effluent output and an influent input;
generate, at said at least one server, control instructions to control said wastewater treatment unit by estimating a state in a state space of said wastewater treatment unit according to a combination of a cost variable value reflecting a treatment cost for treating said at least one influent stream, a time period, said influent flow variable value, said total nitrogen at effluent variable value, said total phosphorus at effluent variable value, and said feedback flow variable value, said control instructions are calculated to optimize a performance of said wastewater treatment unit through at least one of increasing effluent quality and reducing operational costs; and
control, using said control instructions, an operation of at least one of an internal recycle (IR) pump, a flow pump and adaptation of dissolved oxygen level in a reactor of said wastewater treatment unit;
wherein said state space is defined according to a Markov decision process (MDP) framework.

* * * * *